US010856734B2

United States Patent
Palczewski et al.

(10) Patent No.: US 10,856,734 B2
(45) Date of Patent: Dec. 8, 2020

(54) SYSTEMS AND METHODS OF INFRAFRED PSYCHOPHYSICAL MEASUREMENT

(71) Applicant: POLGENIX, INC., Cleveland, OH (US)

(72) Inventors: Grazyna Palczewski, Cleveland, OH (US); Katarzyna Komar, Cleveland, OH (US); Patrycjusz Emplewski, Cleveland, OH (US); Maciej Wojtkowski, Cleveland, OH (US)

(73) Assignee: POLGENIX, INC., Cleveland, OH (US)

( * ) Notice: Subject to any disclaimer, the term of this patent is extended or adjusted under 35 U.S.C. 154(b) by 208 days.

(21) Appl. No.: 15/993,564

(22) Filed: May 30, 2018

(65) Prior Publication Data

US 2018/0271362 A1   Sep. 27, 2018

Related U.S. Application Data

(63) Continuation of application No. PCT/US2016/064197, filed on Nov. 30, 2016.

(60) Provisional application No. 62/261,068, filed on Nov. 30, 2015.

(51) Int. Cl.
| | |
|---|---|
| *A61B 3/00* | (2006.01) |
| *A61B 3/06* | (2006.01) |
| *A61B 3/02* | (2006.01) |
| *A61B 3/024* | (2006.01) |
| *A61B 3/028* | (2006.01) |
| *A61B 3/10* | (2006.01) |

(52) U.S. Cl.
CPC ............... *A61B 3/066* (2013.01); *A61B 3/00* (2013.01); *A61B 3/02* (2013.01); *A61B 3/022* (2013.01); *A61B 3/024* (2013.01); *A61B 3/028* (2013.01); *A61B 3/06* (2013.01); *A61B 3/063* (2013.01); *A61B 3/10* (2013.01)

(58) Field of Classification Search
CPC ........... A61B 3/102; A61B 3/028; A61B 3/10; A61B 3/022; A61B 3/024; A61B 3/00
USPC .................. 351/221, 246, 206, 205, 243
See application file for complete search history.

(56) References Cited

U.S. PATENT DOCUMENTS

| | | | |
|---|---|---|---|
| 8,152,302 B2 * | 4/2012 | Bille | A61B 3/0008 351/246 |
| 2004/0087843 A1 | 5/2004 | Rice et al. | |
| 2007/0121071 A1 | 5/2007 | Jackson et al. | |
| 2010/0262016 A1 | 10/2010 | Imanishi et al. | |

OTHER PUBLICATIONS

Palczewska et al., "Human infrared vision is triggered by two-photon chromophore 1-28 isomerization," PNAS, Dec. 20, 2014.
(Continued)

*Primary Examiner* — Hung X Dang
(74) *Attorney, Agent, or Firm* — Tarolli, Sundheim, Covell & Tummino LLP (57) ABSTRACT

A system for examination of an eye of a subject includes a laser for irradiating a select portion of the retina with a short pulse light having a wavelength of about 800 nm to about 1400 nm at an intensity effective to stimulate two photon induced isomerization of visual pigments in the select portion of the retina of the subject's eye, and an input device to permit the subject to input a reaction or response of the subject to the irradiating light.

28 Claims, 6 Drawing Sheets

(56) References Cited

OTHER PUBLICATIONS

International Search Report for Application No. PCT/US2016/064197.
Written Opinion for Application No. PCT/US2016/064197.

* cited by examiner

SYSTEMS AND METHODS OF INFRAFRED PSYCHOPHYSICAL MEASUREMENT

RELATED APPLICATION

This application is a Continuation of PCT/US2016/064197, filed Nov. 30, 2016, which claims priority from U.S. Provisional Application No. 62/261,068, filed Nov. 30, 2015, the subject matter of which is incorporated herein by reference in its entirety.

BACKGROUND

The retina is comprised of a thin layer of neural cells that line the back of the eyes of vertebrates. In vertebrate embryonic development, the retina and the optic nerve originate as outgrowths of the developing brain. Hence, the retina is part of the central nervous system. The vertebrate retina contains photoreceptor cells (both rods and cones) that respond to light; the resulting neural signals then undergo complex processing by neurons of the retina. The retinal output takes the form of action potentials in retinal ganglion cells whose axons form the optic nerve.

The function of the rod and cone photoreceptors is impacted by the health of the rod and cone photoreceptors themselves. The health and function of the rod and cone photoreceptors are maintained by the retinal pigment epithelium (RPE), the Bruch's membrane and the choriocapillaris (collectively referred to as the RPE/Bruch's membrane complex). The RPE is a dedicated layer of nurse cells behind the neural retina. The RPE sustains photoreceptor health in a number of ways, including, but not limited to, maintaining proper ionic balance, transporting and filtering nutrients, providing retinoid intermediates to replenish photopigment bleached by light exposure and absorbing stray photons. The RPE and the photoreceptors are separated by the choriocapillaris, which provides blood flow to the neural retina.

Impairment of the rod and/or cone photoreceptors may lead to impairment in dark adaptation and other visual processes. Dark adaptation is defined as the recovery of light sensitivity by the retina in the dark after exposure to a conditioning light. In this regard, dark adaptation and other visual processes can essentially be viewed as a bioassay of the health of the rod photoreceptors, the RPE, the Bruch's membrane and the choriocapillaris, and impaired dark adaptation and the impairment of other visual functions may be used as a clinical marker of disease states that impair one or more of the rod and/or cone photoreceptors, the RPE, the Bruch's membrane and the choriocapillaris. For impairments in dark adaptation and other visual processes, such disease states include, but are not limited to age-related macular degeneration (AMD); which is also known as age-related maculopathy (ARM), vitamin A deficiency, Sorsby's Fundus Dystrophy, late autosomal dominant retinal degeneration, retinal impairment related to diabetes and diabetic retinopathy.

SUMMARY

Embodiments described herein relate to systems and methods of infrared psychophysical measurement and to their use in examining the eyes of a subject and monitoring the physiological state of the subject and/or the subject's eye. It was found that humans can detect IR light seen as visual light that arises from two-photon absorption (2PO) and direct isomerization of the retinal chromophore. The perceived wavelength was slightly longer than half of the stimulating IR wavelength. This is consistent with quantum mechanical models for the energetic of two-photon isomerization (2PI). Thus, humans can perceive near IR light via 2PI of visual pigment chromophores. Advantageously, IR excitation of visual pigment chromophores can be used in psychophysical systems and methods of examining the eye and determining and/or monitoring the conditions or pathologies associated with the psychophysical measurement of light.

In some embodiments, a system for examination of an eye of a subject can include a laser for irradiating a selected portion of the retina with a short pulse light having a wavelength of about 800 nm to about 1400 nm at an intensity effective to stimulate two photon induced isomerization of visual pigments in the selected portion of the retina of the subject's eye, and an input device to permit the subject to input a reaction or response of the subject to the light irradiating the selected portion of the retina.

The system can further include a controller capable of recording at least one of the following: a selected portion of the retina irradiated with the light, a reaction of the subject to the irradiating light, a time of the reaction, the intensity of the irradiating light at the time of the reaction, and a wavelength of the irradiating light at the time of the reaction. The controller can determine at least one threshold measurement or partial threshold curve from the recording.

In some embodiments, the controller can compare the at least one threshold measurement or said partial threshold curve to corresponding values from a comparative database comprising a population of individuals, the controller storing said comparative database and the results of said comparing.

The comparative database can be stratified with respect to stratification criteria and the stratification criteria are used to select a defined group of individuals within said comparative database for use in said comparison step. The controller can use the results of the comparison to determine dark adaptation, photopic sensitivity, scotopic sensitivity, visual acuity, contrast sensitivity, color sensitivity, color discrimination, visual field or a combination of the foregoing of the subject.

In some embodiments, the status of the subject is considered impaired if one or more of said at least one threshold measurement or the partial threshold curve meets an impairment criterion. The impairment criterion can be met when the comparing is conducted using a defined group from the comparative database consisting of healthy individuals and one or more of said at least one threshold measurement or the partial threshold curve falls outside of a reference range of corresponding measurements from the defined group. The impairment criterion can also be met when the comparing step is conducted using a defined group from the comparative database consisting of individuals diagnosed with a disease state and one or more of the at least one threshold measurement or said partial threshold curve falls within a reference range of said corresponding measurements from the defined group.

The status of impaired can be indicative of the subject having or at risk for a congenital or late onset retinal degeneration, such as age related macular degeneration, glaucoma, vitamin A deficiency, Sorsby's Fundus Dystrophy, late autosomal dominant retinal degeneration, retinal impairment related to diabetes and diabetic retinopathy.

In some embodiments, the system can include at least one optical element selected from the group consisting of a shaping optic to shape the irradiating light, a directing optic to direct the irradiating light, an optical splitter and a calibration detector. The system can also include a second light source for generating a bleaching light. The second light source can be a light emitting diode, continuous wave (CW) laser, pulsed visible laser, or photographic flash equipped with an electronic strobe.

In some embodiments, the optical power of the irradiating light at a fixed focal volume of the retina is less than 0.2 mW. The laser can have a pulse length in the range of about 10 fs to about 500 ps and a repetition frequency in the range of about 10 MHz to about 120 MHz.

In other embodiments, the system can include an alignment element to ensure the eye of the subject is properly aligned. The alignment element can include at least one of an adjustable chinrest, a target fixation light, a fixation light or a camera to ensure and monitor proper alignment of the eye.

Other embodiments relate to a method for examining the eye of a subject. The method can include irradiating a selected portion of the retina with a short pulse light having a wavelength of about 800 nm to about 1400 nm at an intensity effective to stimulate two photon induced isomerization of visual pigments in the selected portion of the retina of the subject's eye, and monitoring a psychophysical response of the subject to the irradiating light.

In some embodiments, the psychophysical response comprises at least one of dark adaptation, light adaptation, photopic sensitivity, scotopic sensitivity, visual acuity, contrast sensitivity, color sensitivity, color discrimination, visual field or a combination of the foregoing. In other embodiments, the method is used to determine a parameter selected from the group consisting of: the health of the subject's eye, if the subject is suffering from an eye disease, if the subject is at risk for developing an eye disease and the severity of an eye disease.

BRIEF DESCRIPTION OF THE DRAWINGS

FIGS. 2A-B are schematic illustrations embodiment of an optical system in accordance with another embodiment.

FIGS. 5(A-C) illustrate color perception caused by IR laser radiation of the human eye in vivo. (A) Experimental optical setup. AM, adjustable monochromator. (B) Plot showing the results of matching frequency-doubled wavelength perception with the true visible radiation illuminating the retina for 30 healthy volunteers. (C) Reproducibility of results obtained from two healthy volunteers (subjects 1 and 2) for different beam powers at 1040 nm. Points plotted on the graph represent means of matching wavelengths performed by all examined subjects. Error bars in B represent SDs of adjusted wavelengths. Error bars in C are SDs of the means.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

A "patient," "subject," or "host" may mean either a human or non-human animal, such as primates, mammals, and vertebrates.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Portions of the outer segment are routinely shed and regrown in a diurnal process called outer segment renewal. Shed outer segments are ingested and metabolized by RPE cells.

Embodiments described herein relate to systems and methods of infrared psychophysical measurement and to their use in examining the eyes of a subject and monitoring a physiological state of the subject, including the health of the subject's eye, if the subject is suffering from an eye disease, if the subject is at risk for developing an eye disease, and the severity of an eye disease.

It was found that humans can detect IR light seen as visual light that arises from two-photon absorption (2PO) and direct isomerization of the retinal chromophore. The perceived wavelength was slightly longer than half of the stimulating IR wavelength. This is consistent with quantum mechanical models for the energetic of two-photon isomerization (2PI). Thus, humans can perceive near IR light via 2PI of visual pigment chromophores. Advantageously, IR excitation of visual pigment chromophores can be used in psychophysical systems and methods of examining the eye and determining and/or monitoring the conditions or pathologies.

The systems and methods described herein can be used in any psychophysical test or other testing procedure where examination using visual stimuli of a subject's eye is required. The visual stimuli in contrast to previous psychophysical test is provided by an infrared light source that induces two photo isomerization of selected visual pigments in the eye. The infrared light in the indicated range is less prone to age-related changes in absorption of light by lens and cornea than light in the visible range. Visual stimuli include, for example, varying location and intensities of the infrared light, differing infrared wavelengths, differing pulse lengths, differing shapes projected on retina with different refreshing rates to stimulate separately cones and rods etc. Psychophysical tests that can be performed using the infrared visual stimuli include, for example, dark adaptometry, visual sensitivity tests, spatial resolution acuity tests, contrast sensitivity tests, flicker photometry, photostress tests, Vernier acuity tests, colorimetry, motion detection tests, object recognition, and perimetry. Psychophysical tests can be used to assess the status of visual functions including, for example, dark adaptation, photopic sensitivity, scotopic sensitivity, visual acuity, color sensitivity, contrast sensitivity, color discrimination, and visual field. Psychophysical tests can be used to diagnosis the risk, presence or severity of eye diseases including, for example, age-related macular degeneration, vitamin A deficiency, Sorsby's fundus dystrophy, autosomal dominant late-onset degeneration, rod-cone dystrophies, color blindness, ocular tumors, cataract, diabetic retinopathy, and glaucoma.

Advantageously, the methods described herein can be administered in a short time (in as little as 30 minutes or less) in the clinical setting. As a result, healthcare providers will be able to offer the test on a practical and affordable basis, making application of the test and realization of its benefits more widespread. In addition, the burden the test imposes on the subject and the healthcare provider will be significantly reduced. Importantly, the method and systems described herein allows a broader range of subjects to be tested, for instance children or those with impaired cognitive ability. Furthermore, the subject need not have prior exposure to psychophysical test methods.

In addition to its use as a diagnostic tool, the methods and systems described herein can be used to identify the structural, biochemical and physiological changes responsible for the visual dysfunction and the progression of the disease states, such as, but not limited to, congenital or late onset retinal degeneration, such as age related macular degeneration, glaucoma, vitamin A deficiency, Sorsby's Fundus Dystrophy, late autosomal dominant retinal degeneration, retinal impairment related to diabetes, and diabetic retinopathy. This is particularly useful since many of such disease states are currently believed to be a heterogeneous rather than a unitary genetic phenomenon and thus may have a variety of clinical manifestations depending on the underlying cause. By the early and accurate identification of those individuals at risk for developing diseases, such as macular degeneration and the other disease states, discussed herein (by virtue of their identification as having impaired visual perception) the structural, biochemical and physiological changes can be identified and correlated with various stages of disease state progression. Such information can be used to design theoretical models of the disease state, evaluate animal models of the disease state and to identify new opportunities for therapeutic intervention in the treatment of the disease state.

In the methods described herein, a selected portion of the retina of the subject's eye can be irradiated with a short pulse light having a wavelength of about 800 nm to about 1400 nm at an intensity sufficient to stimulate two photon induced isomerization of visual pigments in the selected portion of the retina of the subject's eye. The psychophysical response or reaction of the subject to the light irradiating the selected portion of the retina can then be measured and compared to a control to determine the health of the subject's eye, if the subject is suffering from an eye disease, if the subject is at risk for developing an eye disease and the severity of an eye disease. The psychophysical response can include at least one of dark adaptation, photopic sensitivity, scotopic sensitivity, visual acuity, contrast sensitivity, color sensitivity, color discrimination, visual field or a combination of the foregoing.

In some embodiments, a selected portion of a mammalian retina can be irradiated, in vivo, with light having a wavelength in the range of about 800 nm to about 1400 nm, for example, about 950 nm to 1100 nm, or from about 1000 nm to 1100 nm at an intensity effective to stimulate two photon induced isomerization of visual pigments in the selected portion of the retina of the subject's eye.

In some embodiments, the subject undergoing testing is subject to a bleaching protocol. The bleaching protocol may be varied as is known in the art. The bleaching protocol adapts the test eye to a light of a first luminance level (by desensitizing a portion of the rhodopsin molecules in the test eye on exposure to the light of a first luminance level). Visual recovery (i.e., dark adaptation) is then measured as the test eye adapts to a light of a second luminance level. Therefore, the first luminance level serves as a standardized baseline from which visual recovery is measured. Any bleaching protocol that provides this standardized baseline may be used in the method and system described herein. The light of the first luminance level may be an intense light, such as that provided by light emitting diode, continuous wave (CW) laser or flash, and the light of the second luminance level may be at or close to 0 cd/m$^2$, such as would occur in a dark room. Alternatively, the light of the first luminance level may be a light produced by an ordinary light bulb or by the ambient light in a room, and the light of the second luminance level may be at or close to 0 cd/m$^2$, such as would occur in a dark room.

Many light delivery methods can be used to deliver the light of the first luminance level (which is referred to hereafter as the photobleaching light), such as photographic flashes, adapting fields, illuminated backgrounds, direct projection into the eye, exposure to ambient light, or staring into a light bulb. As discussed above, there are numerous possibilities. Classically, subjects viewed an adapting field to bleach the photopigment. Another method of bleaching is to project light into the eye using a Maxwellian view system.

Because the light exposure is brief and can be localized outside the fovea, it is not irritating to the subjects and the subjects do not need to maintain fixation for long period of time. With proper patient instructions blinking is not an issue.

The bleaching protocol can desensitize the desired amount of rhodopsin molecules and provides a standardized baseline to measure visual recovery to the second luminance level. The intensity of the bleaching light or the time of exposure to the bleaching light can be modulated to produce the desired amount of desensitization. In one embodiment, an equivalent of about 50% to 100% of the rhodopsin molecules is desensitized. The intensity of the bleaching light can be adjusted to desensitize the appropriate amount of rhodopsin molecules.

After the bleaching protocol, visual recovery to the second luminance level is monitored. This recovery of light sensitivity is mediated primarily by the retina and measures predominately rod-mediated sensitivity. The subject provides a series of responses or reactions to the short pulse irradiating light, which is used to generate one or more index factors. The index factors can be used in a comparison step to determine a dark adaptation status of the subject. In one embodiment, the response of the subject is used to determine a threshold measurement. During threshold measurements, the selected portion of the retina of the subject's eye is irradiated with the short pulse light. A variety of classical methods can be used to determine the threshold measurement, including but not limited to method of limits, just noticeable difference, and method of adjustment. These techniques are well known in the art.

Thresholds measurements can be sampled in such a way as to provide sufficient data to fit models of dark adaptation. In one embodiment, threshold measurements are sampled once every 1 to 5 minutes. Another embodiment would be to sample as fast as possible according to subject abilities. Another embodiment would be to sample threshold measurements twice every minute. Yet another embodiment would be to sample 2 threshold measurements per minute early during the test then sample 1 threshold measurement every 2 minutes thereafter. Higher or lower sampling rates may be used as desired to balance the need of producing an adequate dark adaptation function for model fitting against subject burden.

The threshold measurements may be used to generate a full or a partial dark adaptation threshold function/curve. In such a threshold function/curve, one or more threshold measurements (which indicate sensitivity of recovery) are plotted as a function of time to generate the dark adaptation function/curve. Various scales for the sensitivity measurement may be used, such as a semi-log unit scale. The curve is not required to be generated, but may be helpful as a visual tool to aid the healthcare provider.

The obtaining of thresholds measurements may be terminated based on a decision rule. A number of decision rules are possible. For example, threshold measurements may be terminated after defined period of time has elapsed, when the subject's visual sensitivity ceases to change over a defined period of time or when the subject's sensitivity returns to a previously obtained baseline value measured prior to bleaching. Additionally, threshold measurements may be terminated if a specific dark index factor, such as an adaptation parameter, does not appear within a defined period of time on the inability to fit the threshold measurements to an appropriate model of dark adaptation, or on the failure to make a sufficiently close match to the comparative database.

The threshold measurements obtained as discussed above may be directly compared to the comparative database or may be applied to an appropriate dark adaptation model. A variety of models may be used. These include models with one component or more than one component. Examples of models that may be used include, but are not limited to, a one-linear, one-exponential model, a bi-linear model, and a tri-linear model. In one example of a two-component model, one component models the cone photoreceptors and one component models the rod photoreceptors. When more than two components are used in the model, the rods or the cones may be analyzed by the additional components of the model.

Dark adaptation parameters, individual threshold measurements or other data may be extracted from the modeled data without providing a graphical threshold curve. Key dark adaptation function parameters that can be extracted from the model fit include, but are not limited to, the rod-cone break time, the rod intercept and the rod recovery time constant.

The threshold measurements may be applied to an appropriate model fit as the threshold measurements are generated, after all threshold measurements are obtained or after a determined number of threshold measurements are obtained. For example, every time a valid threshold measurement is obtained, the threshold measurements may be applied to an appropriate dark adaptation model to determine if a threshold model fit can be achieved. Using this approach, the model may be generated instantaneously as the test progresses. In addition, if a model fit is not achieved in a predetermined amount of time (such as 5-10 minutes, the time point at which the rod-cone break should appear in a healthy individual), the threshold measurements may be terminated and the subject considered to have impaired dark adaptation. Alternatively, all threshold measurements may be obtained before the threshold measurements are applied to an appropriate model.

From the threshold measurements and the data generated during the modeling step, an "index factor" may be extracted. The index factor may be a threshold curve generated by the appropriate model from the threshold measurements, a partial threshold curve generated by the appropriate model from the threshold measurements, individual threshold measurements selected from the appropriate model, individual threshold measurements selected prior to modeling, a dark adaptation parameter determined from the appropriate model, or any combination of the foregoing. One or more index factors may then be compared with corresponding index factors determined from healthy individuals to determine the dark adaptation status of the subject.

The dark adaptation parameters can include, for example, the time constant of the cone-mediated sensitivity recovery, the time constant of rod-mediated sensitivity recovery, the cone plateau, the rod plateau, the rod-cone break, the rod intercept, and the duration from the bleaching to the final threshold measurement.

The dark adaptation parameters above are, with the exception of the rod intercept, described and known in the art and have the meanings known to one of ordinary skill in the art.

The individuals in the comparative database may be aged matched to the subject, or may be non-aged matched as compared to the subject. For example, if the subject is 65 years of age, in one embodiment the comparative database may be composed of individuals with ages from 60 to 70 years, or in a second embodiment, the comparative database may be composed of individuals with ages from 25 to 40 years. The use of a comparative database comprising a younger population may offer certain advantages since the younger subjects that comprise the population will be more likely to be free of disease states and other conditions that may impact their dark adaptation.

The individuals making up the comparative database may be healthy (i.e., disease free) or they may be selected based on their diagnosis with AMD or any of the other disease states which have impaired dark adaptation or visual acuity as a clinical manifestation, or both. If healthy individuals are selected, the index factors determined from the subject can be compared with the corresponding index factors for the healthy individuals. If individuals with a diagnosed disease state are selected, the index factors determined from the subject can be compared with the corresponding index factors for the individuals diagnosed with a disease states and/or defined stages of a disease state. In this manner, the comparison may be able to predict if the subject has impaired dark adaptation (from a comparison with healthy individuals in the comparative database), is suffering from a disease state (from a comparison with individuals in the comparative database diagnosed with said disease state) or to diagnose the severity of the disease state (from a comparison with individuals in the comparative database diagnosed with said stage of the disease state). For example, if the disease state is AMD, the index factors determined for the subject may be compared to corresponding index factors from individuals in the comparative database who are diagnosed with early, intermediate or late stage AMD. The stratification of the database, as discussed below, may aid in making such comparisons.

The comparative database may be stratified based on a number of stratification criteria. These criteria may be dark adaptation status, risk factors, demographic factors, other relevant factors or a combination of the preceding. Examples, of risk factors include, but are not limited to, age, smoking status, body mass index, and status with regard to health conditions (for example diabetes and AMD status). Other risk factors may also be included. Demographic factors include, but are not limited to, lens density, gender and ethnicity. The inclusion of a specific stratification criteria as a risk factor or demographic factor may be modified (for example, age may be considered both a risk factor and a demographic factor). The individuals in the comparative database may be tagged or otherwise identified, such that the appropriate population of individuals in the comparative database may be selected for the comparison to the subject.

Furthermore, the comparative database may be refined over time. The individuals in the database may be followed over time and their health status monitored. If an individual no longer meets an inclusion criterion for the comparative database, the individual may be removed. The inclusion criteria may be development of a disease state or impaired dark adaptation within a defined time period of the inclusion of the individual in said comparative database.

One or more of these index factors is then compared to the corresponding index factors obtained from appropriately selected individuals in a comparative database. Appropriately selected means that the index factor from a defined group of individuals in the comparative database is selected for comparison to the index factor from the subject. The defined group may be all the individuals in the database or less than all the individuals in the comparative database. The defined group may be selected on the basis of stratification criteria as discussed above. The healthcare provider may select the defined group, with such selection based on one or more defining characteristics of the subject. For example, if the subject is a 60 year old, non-smoking, Caucasian male suspected of having AMD, the stratification criteria may be used to select the defined group from the comparative database for the comparison step. In one embodiment, the defined group may be selected on the basis of ethnicity (Caucasian), gender (male), health status (disease free or diagnosed with ARMD), and age (20-45 years of age). Furthermore, the comparison may be carried out multiple times for any given subject to various iterations of the comparative database. For example, given the same 60 year old, non-smoking, Caucasian male subject suspected of having AMD, a second comparison could be made using a defined group from the database selected on the basis of gender (male) only, or selected to include all individuals in the comparative database.

The comparison may be made to the absolute value of the appropriate index factor or to a normal reference range of the appropriate index factor from the comparative database to determine a dark adaptation status of the subject. The normal reference range is a statistical range about said index factor. In one embodiment, the statistical range is the mean of the values for the selected index factor from the comparative database .+-.two standard deviations of the mean; other statistical ranges may also be used. If the index factor determined for the subject satisfies an "impairment criteria" the subjects is considered to have an impaired status. If the index factor determined for the subject does not satisfy an "impairment criteria" the subjects is not considered to have an impaired status.

The impairment criteria may vary depending on the nature of the defined group selected from the comparative database for the comparison step. If a comparison is made to a defined group of healthy individuals from the comparative database, the impairment criteria is satisfied if one or more of the index factors determined for the subject fall outside of the normal reference range for the corresponding index factors in the comparative database. In this case, the subject is considered to have an impaired status and to be at risk for AMD and the other disease states described herein. If a comparison is made to individuals from the comparative database having a diagnosed disease state and/or a specific stage of a disease state, the impairment criteria is satisfied if one or more of the index factors determined for the subject fall within the normal reference range for the corresponding index factors in the comparative database.

In addition, the method disclosed may incorporate certain "compensation strategies". These compensation strategies may be used to account for variations in lens density, pupil size and other confounding factors that may impact the results of the method.

The exact form and nature of the system for conducting the method described herein may vary, as would be known to one of ordinary skill in the art. An exemplary arrangement of an apparatus capable of applying the method described herein is provided below. The apparatus may be modified and altered as would be obvious to one of ordinary skill in the art without deviating from the teachings disclosed herein.

In its most basic form, the system includes a laser for irradiating a selected portion of the retina with a short pulse light having a wavelength of about 800 nm to about 1400 nm at an intensity effective to stimulate two photon induced isomerization of visual pigments in the selected portion of the retina of the subject's eye, and an input device to permit the subject to input a reaction of the subject to the irradiating light to convey to the healthcare provider information regarding the irradiating light (such as that the irradiating light is visible or the irradiating light is not visible). Other functions may be incorporated into the apparatus, such as a means for irradiating different portions of the subject's retina, a means for bleaching the test eye, a means for aligning the test eye, a means for confirming alignment and similar items.

In one embodiment, the laser can be a component of a laser scanning microscope or, for example, a component of a scanning laser ophthalmoscope. By way of example, a commercially available laser scanning microscope can be modified to illuminate the retina of a mammalian eye.

The laser can have a repetition frequency in the range of, for example, from 10 MHz to 120 MHz, a pulse length in the range of, for example, from 10 femtoseconds to 500 ps, such as from 100 fs to 400 fs. The laser light can be scanned over a portion of a human retina (e.g., scanned vertically, and/or scanned horizontally, and/or scanned in a regular and/or irregular geometric pattern), or directed onto a defined area of the retina without scanning. The amplitude mask placed in optical path of scanning can allow for additional modification of projected pattern. The placing of chopper or optical modulator in beam path can allow for modulated in time stimulation of the retina.

Advantageously, the system is designed and operated such that the laser power entering the pupil will not exceed the maximum permissible radiant power for scanning laser beam measured per American National Standard, ANSI Z136.1 calculated on the basis of for exposure time 30 minutes.

A variety of optical elements may be used in various combinations to determine the properties of the light beam. These include directing means to direct the light beam, refining means to collimate and shape the light beam, selecting means to select the desired spectrum of the light beam, and modulating means to control the intensity of the light beam. In one embodiment, the directing means are mirrors, the refining means is shaping optics, the selecting means is an optical filter, and the modulating means is a neutral density filter or an electronic modulator. Additional optical elements may also be incorporated, such as an optical splitter to direct a portion of the light beam to a calibration detector to record the characteristics of the light beam and to ensure the characteristics of the light beam are as desired. The target spot is then directed to a means for display, which may be a screen or other visual display.

The system may be portable or fixed in a permanent location. In one embodiment, the subject may be confined in a testing booth and the system may be a part of the testing booth or placed in the testing booth. The healthcare provider may be located outside the testing booth to supervise the operation of the apparatus. An advantage of this embodiment is that the healthcare provider will be in normal light during the implementation of the method and can better monitor the method.

Figure 1:
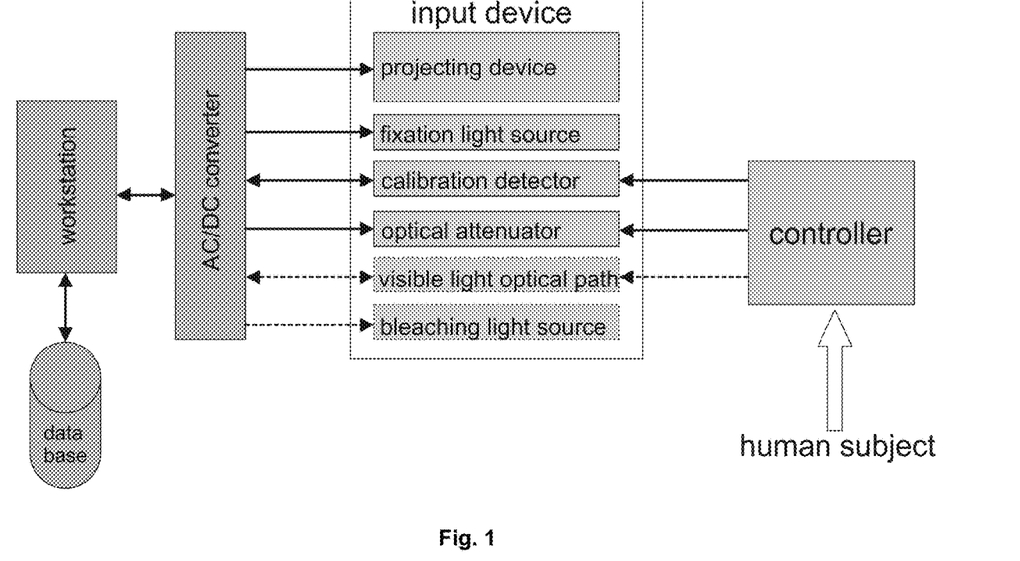
FIG. 1 is schematic illustration of an optical system in accordance with one embodiment.

FIG. 1 illustrates a schematic diagram of an optical system in accordance with embodiments described herein. The optical system includes an input device that comprises a projecting device, fixation light source, calibration detector or device, and optical attenuator. The visible light source optical path and bleaching light source are present in some embodiments only. The system is controlled by workstation computer through, for example, an AC/DC converter. Data measured from calibration device (e.g., power of the beam and/or time point of measurement) and visible light optical train (e.g., wavelength) can be readout and stored in computer memory. The human subject can interact with the device by controller such that he/she can, for example, provoke measurement by the detector, attenuation of infrared beam or changing the wavelength of visible light. The obtained data can be stored in database and can be compared with previously collected results.

Figure 4:
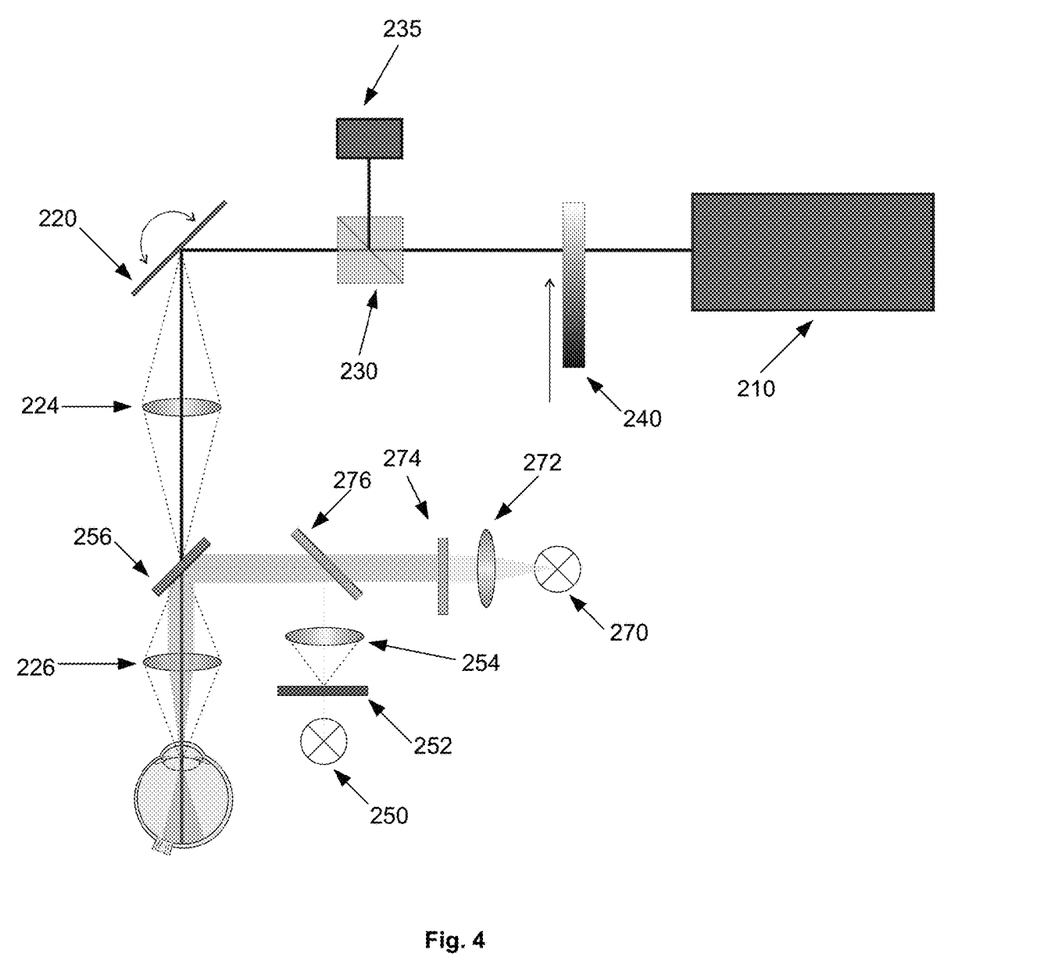
FIG. 4 is a schematic illustration of an optical system for dark adaptation recovery measurements in accordance with another embodiment.

In some embodiments, as shown schematically in FIG. 4, the system can include a second light source for photobleaching the subject's eye prior to irradiating the subjects eye with the short pulse infrared laser. The second light source can include, for example, a light emitting diode that supplies a 530 nm.

In each embodiment, light beam from pulsed infrared laser and/or the second light source can be acted upon by one or more optical elements. These optical elements include, but are not limited to, directing means to direct the light beam, refining means to collimate and shape the light beam, selecting means to select the desired spectrum of the light beam, and modulating means to control the intensity of the light beam. In one embodiment, the directing means are mirrors, the refining means are shaping optics, the selecting means is an optical filter, and the modulating means is a neutral density filter or an electronic modulator.

The controller can be in communication with the various components of the system, such as, but not limited to, the pulsed infrared laser, bleaching light source, the infrared light source, the directing means, the refining means, the selecting means, and the modulating means. In addition, the controller may be in communication with the calibration detector and the subject input device (as described below). For example, the controller may control the light emission from the light source so that the pulses of light emitted by the light source correspond to the configuration required by the test method and emissions from the bleaching light source to ensure that the percent bleaching desired is obtained.

In addition, the controller is capable of adjusting the parameters of the components of the system as dictated by the method described. Furthermore, the controller can also record the status and output of each of the components of the apparatus. For example, the controller may record the intensity of the pulsed infrared laser. The controller can also record the input from the subject input device, which is used to allow the subject to input his/her responses or reactions to the pulsed irradiated light, for use in generating the threshold values. The controller may further measure and record the time elapsed during the implementation of the method (e.g., timing to start in one embodiment immediately after the bleaching step is accomplished) and the time at which subject inputs are received from the subject input device and the time at which the various parameters of the method are changed (such as the changing intensity of the pulsed irradiating light). By comparing the timing of the subject response to the target stimulus as received from the subject input device and correlating the subject responses to the status of the parameters of the apparatus, the controller may then determine and record the threshold measurements and execute calculations required for noise reduction in the threshold measurements.

A means for comparison may be in communication with the controller. The means for comparison may be separate from or integral with the controller. The means for comparison may use the threshold measurements and the information from the components of the system for subsequent analysis. The means for comparison may be capable of executing calculations to fit the threshold measurements, such as to a desired model of dark adaptation and generating a full or partial dark adaptation model fit and/or the desired index factors from said threshold measurements and then recording and storing said information. As discussed above, the means for comparison may execute such calculations as the threshold measurements are collected, or may execute such calculations after all desired threshold measurements are obtained. The means for comparison may be an external device in communication with the controller via the internet.

The measured threshold measurements or optionally the index factors, such as the dark adaptation parameters, may then be compared to corresponding threshold measurements or index factors in a comparative database and the result recorded and stored. The comparative database threshold measurements and comparison results may be contained within the means for comparison allowing the process to be automated or may be separate from and in communication with the means for comparison. The means for comparison may output the information to a visual display as desired. The output may be in the form of a full or partial threshold curve and model fit or other graphical format. In addition, the individual threshold measurements may be displayed as well. The output may be further conveyed to a storage device or an output device, such as a printer.

Figure 2A:
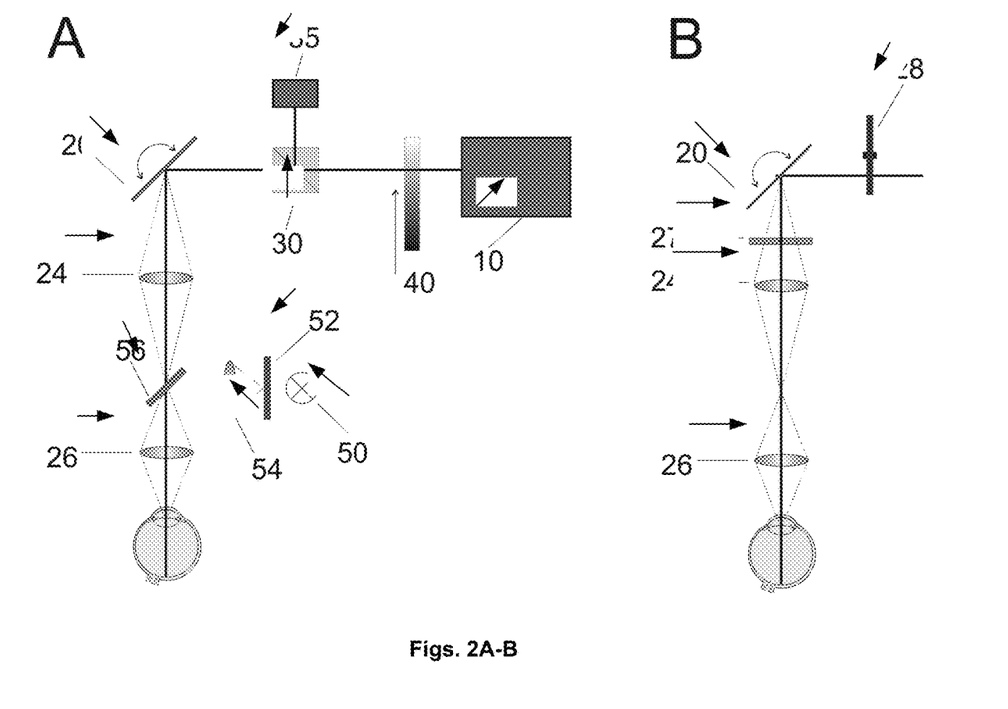
Figure 3:
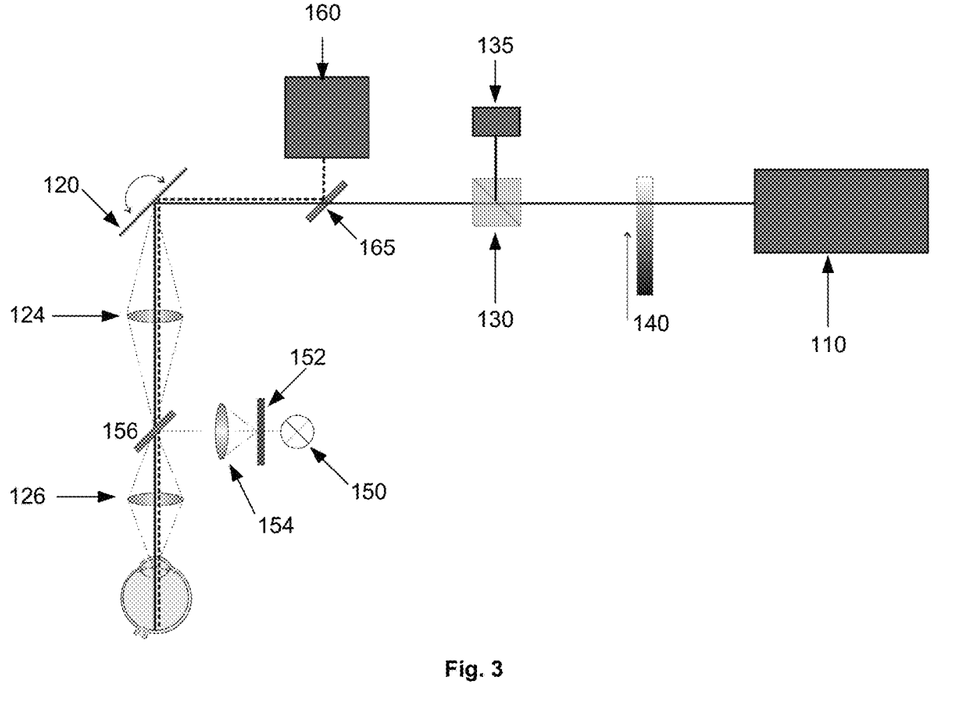
FIG. 3 is schematic illustration of an optical system for perceived wavelength measurements in accordance with another embodiment.

Schematic illustrations of optical systems in accordance with embodiments described herein are shown in FIGS. 2-4. FIG. 2 shows a basic embodiment of an optical system described herein. The system can include a stimulating laser 10; an input device that includes a projecting device (elements 20-26 in (A) or 20-28 (B) of the system); a beamsplitter 30 and calibration detector (power meter) 35; an optical attenuator (gradient neutral density filter) 40; a fixation optical train that includes a red light source 50 (e.g., >620 nm), a dark plate with a transparent fixation pattern 52, a lens 54, pellicle or dichroic to combine fixation into main optical path of the instrument 56. Two versions of the projecting device are shown. Version (A) includes a pair of scanning mirrors 20 and a 4-f lens system 24 and 26. Version (B) includes the addition of amplitude mask 27 and chopper 28 for modulated stimulation of the retina. The subject in accordance with this embodiment can attenuate the laser beam by changing the position of the optical attenuator 40 and measure its power with the calibration detector 35 by using the controller.

FIG. 3 is a schematic illustration of an example of an optical system for perceived wavelength measurements in accordance with another embodiment. The optical system in accordance with this embodiment includes a stimulating laser 110; an input device that includes a projecting device, that includes a pair of scanning mirrors 120 and 4-f lens system 124 and 126; a beamsplitter 130 and calibration detector (power meter) 135; an optical attenuator 140; a fixation optical train consisting of red light source (e.g., >620 nm) 150, a dark plate with transparent fixation pattern 152, a lens 154, a pellicle or dichroic to combine fixation into main optical path of the instrument 156, a source of visible light with known wavelength at output 160 (e.g., it can be a bulb filtered by adjustable monochromator or visible source of known wavelength, such as another laser or laser diode), and a dichroic mirror 165. The subject can attenuate the laser beam by changing the position of the attenuator 140, measure its power with the calibration detector 135 and change the wavelength (if it is tunable) of visible light at output 160 by using the controller.

FIG. 4 is a schematic illustration of an example of an optical system for dark adaptation recovery measurements in accordance with another embodiment. The optical system in accordance with this embodiment includes a stimulating laser 210; an input device comprising: projecting device, that includes a pair of scanning mirrors 220 and a 4-f lens system 224 and 226; a beamsplitter 230 and a calibration detector (power meter) 235; an optical atenuator 240; a fixation optical train that includes a red light source (e.g., >620 nm) 250, a dark plate with transparent fixation pattern 252, a lens 254, a pellicle or dichroic to combine fixation and bleaching into main optical path of the instrument 256, a bleaching light source 270, lens 272, transmission filter 274, hot mirror 276. The bleaching light of known intensity is turned on for defined time period before measurements. The subject can attenuate the laser beam by changing the position of attenuator 240 and measure its power with the calibration detector 235 by using the controller, alternatively variable strength timuli will be displayed on subject retina and subject task would be to indicate when he/she can see the stimuli Other configurations containing additional elements or similar substitutions for the elements described may be envisioned. In addition, the order of the elements described may be re-arranged as desired.

In some embodiments, the optical system can further include an eye tracking system and/or gaze tracking system configured to acquire eye and/or gaze tracking data from the subject. The eye tracker may be a device for measuring eye movement of the subject, which may be based on an optical tracking method using a camera or an optical sensor, electrooculogram (EOG) method, etc. The eye tracker may be any one of non-wearable eye trackers and wearable eye trackers.

In some embodiments, the eye tracker can be configured to modulate the laser such that the laser is able irradiate selected portions of the retina with a short pulse light having a wavelength of about 800 nm to about 1400 nm at an intensity effective to stimulate two photon induced isomerization of visual pigments in the selected portion of the retina of the subject's eye during movement of the subjects eye.

In other embodiments, the eye tracker can provide subject inputs and the time at which the various parameters of the method are changed (such as the changing intensity of the pulsed irradiating light). By comparing the timing of the subject response to the target stimulus as received from the eye tracker and correlating the subject responses to the status of the parameters of the apparatus, the controller may then determine and record the threshold measurements and execute calculations required for noise reduction in the threshold measurements.

In some embodiments, the gaze tracking system tracks eyes of the patient using a retinal tracking system and an anterior segment tracking system. The gaze tracking system can image and track the retina and registering a location of the stimulus with the short pulse light having a wavelength of about 800 nm to about 1400 nm at an intensity sufficient to stimulate two photon induced isomerization of visual pigments in the selected portion of the retina of the subject's eye.

In some embodiments, the operation of the system and execution of the method can be viewed as having the following steps: 1) aligning the subject; 2), photobleaching of the test eye; 3) monitoring recovery of visual sensitivity (i.e. scotopic recovery); 4) optionally fitting the data obtained to an appropriate model to generate the dark adaptation parameters; and 5) comparing the threshold measurements or optionally the index factors, such as the dark adaptation parameters, from the subject to a comparative database. The steps should not be construed as limiting descriptions, but are simply convenient areas for further detailed discussion. Each of these steps will be discussed in greater detail below. Furthermore, the hardware required to carry out each of these steps need not be incorporated into the test apparatus, but may be if desired.

In some embodiments, the optical system and methods can include a structural evaluation unit recording one or more structural measurements associated with the retina of the subject. The structural evaluation unit can be configured for scanning laser ophthalmoscopy in addition to psychophysical testing or combined with scanning laser ophthalmoscopy (SLO) device, optical coherence tomography device (OCT), and/or polarization sensitive scanning laser ophthalmoscope (PS-SLO) so that the exact location of the sensitivity or two photon isomerization can be more readily measured and features of the eye, such as vasculature, can be detected. For example, a two-photon ophthalmoscope with integrated IR sensitivity measurements and SLO imaging can apply pulsed 1045 nm laser light to test sensitivity and 800-980 nm light to provide SLO imaging of the back of the eye. The SLO image will span up-to 50°×50° on the retina, with 112×112 to 2090×2090 pixels and the scanning speed of up to 25 frames per second. The SLO can operate in the reflectance mode. SLO and sensitivity testing can be synchronized such that exact location of the sensitivity trace can be indicated in the image. The instrument will allow for the selection of the location of sensitivity trace anywhere within the field of view of the SLO. The SLO will provide images of vasculature.

In one or more embodiments, such function may be implemented using two separate devices and registering results of the psychophysical testing and structural evaluation by comparing and registering respective fundus images recorded by the two separate devices. In other embodiments, the evaluation may be performed on a single device and the registration may come from an intrinsic alignment of the structural and psychophysical testing modules within the device.

Example 1

In this Example, we show that humans can see IR radiation through 2PO absorption and direct photoisomerization of visual pigment molecules in rod and cone photoreceptor cells.
Methods
Human Psychophysics
Methods Visual perception caused by IR light in the human eye was investigated in vivo. All tests were conducted in compliance with American National Standard Institute (ANSI Z136.1) and European Standards (EN 60825-1) providing recommendations for permissible exposure limits of laser light. We also implemented safety procedures described in the literature for ophthalmic devices, especially scanning laser ophthalmoscopes and fundus autofluorescence devices. The study was approved by the Ethics Committee of the Collegium Medicum in Bydgoszcz, Nicolaus Copernicus University in Torun, Poland. Examinations were carried out only after written informed consent was obtained.

The human psychophysics experiments were performed under dark room conditions. At the level of the subject's eye, the average luminance was 0.6 lx. The optical setup was isolated from residual ambient light by its dedicated housing. In the optical setup, we included a cutoff filter (Chroma T750lpxxr) to ensure that there was no leakage of the pump laser frequency. During spectral sensitivity experiments, a subject's head was covered by a black curtain attached to the housing. Before sensitivity testing, all human subjects were dark adapted in low light (0.6 lx) conditions for 2 h and then for another 20 min under this black curtain.

Color matching experiments were performed to determine an individual's perception of color associated with a given frequency-doubled wavelength during scanning of his/her retina by an IR femtosecond laser beam.

The test was performed on the left eyes of 30 healthy volunteers aged 21-38 y, both males and females. We constructed a simple experimental optical setup that included modifications derived from earlier experiments. Dmitriev and colleagues had used 20-ns pulses and localized constant patterns projected onto the retina. Here we used 200-fs (76-MHz repetition rate) laser light pulses ranging from 950 to 1200 nm generated by an optical parametric amplifier (OPO) (Emerald; APE), except for a 1040-nm light originating directly from the laser pumping OPO (Femtotrain; HighQLasers). Estimated length of pulses at the cornea was in the picosecond range due to dispersive broadening in the fibers and optical setup. Instead of projecting large patterns, we focused the beam onto a 20-μm spot in the retina.

Beam power measured on the cornea was equal to 1 mW for beams spanning 950-1125 nm and 1.5 mW for those covering 1150 and 1200 nm, well below ANSI and EU standards for maximum permissible power (MPΦ) (American National Standard for Safe use of Lasers; ANSI Z136.1). Calculations of MPΦ were performed using a stationary beam. The single pulse model at 950 nm yielded 1.39 W (at 1100 nm, 4.39 W; at 1200 nm, 34.9 W). The average power heat buildup model at 950 nm gave a MPΦ of 1.21 mW, and at 1100 and 1200 nm were 1.93 and 153 mW, respectively. To provide an increased safety margin, we added a beam scanning system that provided full control over the intensity of optical radiation power delivered to the eye as a function of time.

Figure 5A:
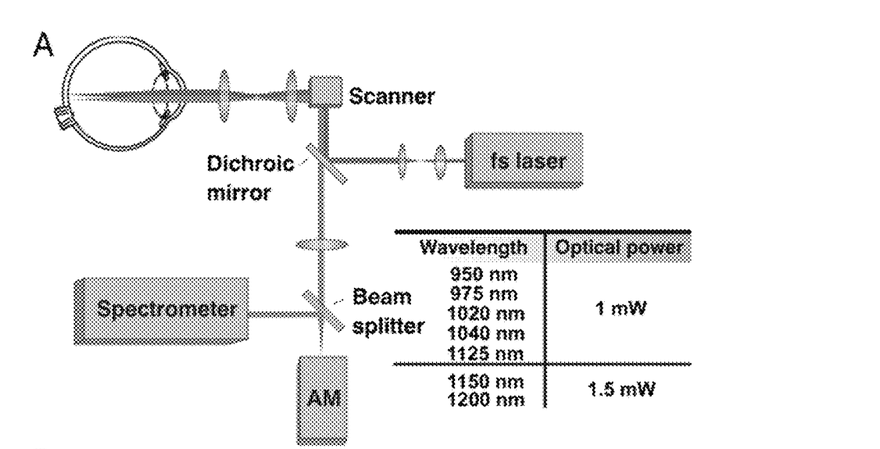

The laser beam was directed to the retina by a pair of IR galvoscanners that created a single linear scan on the fundus perceived by the volunteer as a single horizontal line. In close proximity to this line, we projected a similar shaped horizontal line of visible radiation originating from a halogen lamp and transmitted through a monochromator (spectral width of 8 nm). Volunteers then were asked to match the colors of the two lines by manually adjusting the wavelength of the second line projected onto the retina via the monochromator. The wavelength of the beam from the monochromator was measured independently by a spectrometer. A schematic for this setup is shown in FIG. 5A.

The system includes a pulsed infrared laser that can provide 200-fs (76-MHz repetition rate) laser light pulses ranging from 950 to 1200 nm generated by an optical parametric amplifier (OPO) (Emerald; APE). The laser beam is directed to the retina by a pair of IR galvoscanners that created a single linear scan on the fundus perceived by the subject as a single horizontal line. The system can also project a similar shaped horizontal line of visible radiation originating from a halogen lamp and transmitted through a monochromator (spectral width of 8 nm). The system also includes monochromator that can be manually adjusted by the subjects using an input device and controller to match the colors of the two lines of the second line projected onto the retina. The system further includes a spectrometer to independently measure the wavelength of the beam.

A 20-μm scanning beam enabled the extraction of many photoreceptors simultaneously. For example, 15-60 cones were excited by the beam as a function of retinal location.

In our study almost all points are above the double frequency line. The explanation may involve a significant difference in the quality of the experimental setup. In 70 ties there was no chance to have enough density of photons (pulses short enough) to project anything on the retina. We used a focused beam of well-controlled optical exposure with much shorter pulses providing a five order of magnitude difference in the initial pulse length. (Taking into account pulse stretching caused by dispersive elements in the optical setup and the human eye, this pulse was still at least 10000 times shorter in our experiments). With these experimental settings, it was very easy to see the signal generated by IR radiation, even in ambient light. A high repetition rate of the laser ensured that we should be far from the frequency range responsible for color illusions, which are usually in the range of hundreds of hertz.

Figure 6:
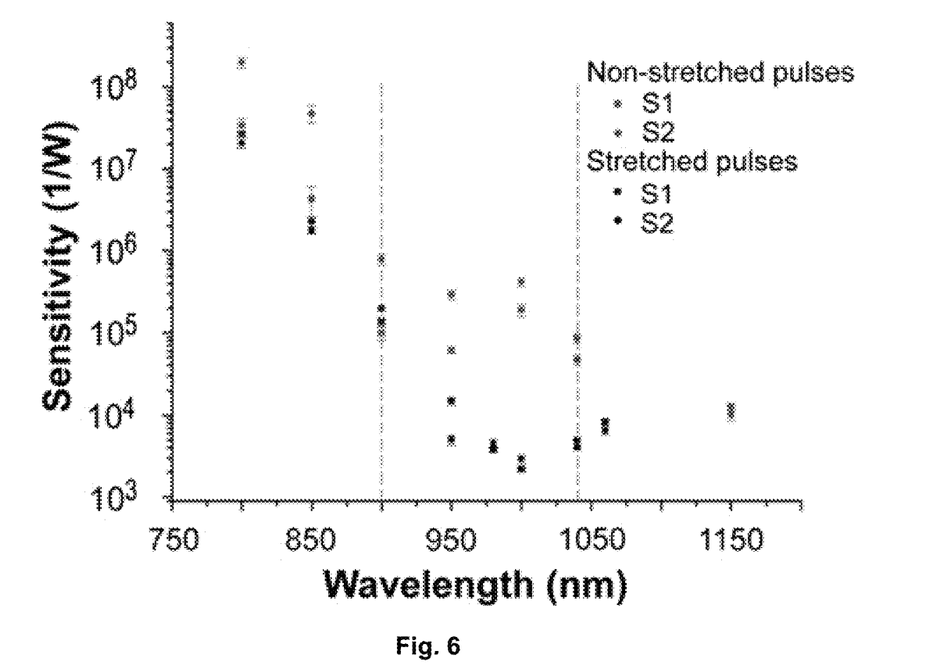
FIG. 6 illustrates a nonlinear process contributes to spectral sensitivity of human visual perception. Spectral sensitivity data obtained with 0.3- to 0.6-ns (long) laser pulses are shown in black and the spectral sensitivity data obtained with 0.5- to 1.25-ps (short) laser pulses are in grey. Dashed vertical lines separate regions of wavelengths with different color perception. Measurements were taken on two healthy dark-adapted subjects (S1 and S2). Each point represents the average of 10 measurements.
Figure 7:
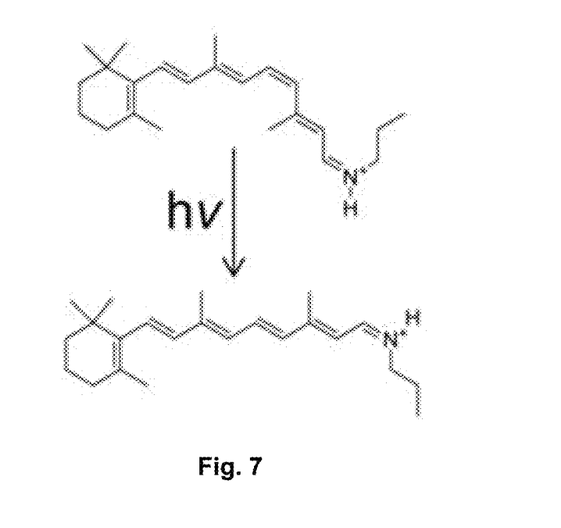
FIG. 7 illustrates IR isomerization of model visual pigments. Chemical formulas of the protonated Schiff base. (Upper) 11-cis-propylamine Schiff base. (Lower) All-trans-propylamine Schiff base.

Measurements of spectral sensitivity (FIG. 6) were made with a modified experimental optical setup compared with the one shown in FIG. 5. Modifications were as follows: (i) the reference arm, including the monochromator (AM) and a spectrometer, was blocked; (ii) the dichroic mirror was replaced by a beam-splitter to divide the beam and direct a defined portion of the beam (~33%) onto the laser power meter connected to a personal computer (PC); (iii) to obtain long pulses, the laser beam was routed through 1 km of a fiber spool (Corning HI780); and (iv) an adjustable neutral gradient filter was placed at the output of the laser. To measure minimal power of the laser beam that still caused a visual sensation, this filter was adjusted by the subject during the test procedure. After careful calibration, the optical power recorded by the PC corresponded to the optical power of the IR beam reaching the cornea. Values measured by the power meter were saved in PC memory after the tested subject pressed a mouse button. Both tested subjects were healthy volunteers: S1, a 37-y-old woman; S2, a 34-y-old man.

To achieve the best viewing comfort for a subject, the laser beam illuminating the retina also scanned along a horizontal line. The edges of this line (corresponding to scanner turnout points) were blocked by a diaphragm placed in the focal plane of the first lens after the scanners. Measurements were repeated 12 times (on further analysis, 10 values were used after rejection of 2 extreme values). Then the wavelength of the OPO light source was changed into the next one. Measurements started from short wavelengths to long. If a subject needed to "take a break" during testing, the tested eye was covered by a black patch before he/she emerged from under the black curtain back into dark room conditions.

Measurements with both short and stretched pulses were performed within 2 d. Repeatable localization of the beam on the retina was assured by fixation of the chinrest with respect to the objective. Additionally, the central position and length of the projected pattern (line) also served to achieve fixation: the entire line was projected onto the retina only when the scanning pivot point was in the central position of the eye pupil. Both long and short pulses were affected by the dispersion of the optical system. Elongation of pulses in the time domain was estimated assuming a Gaussian pulse and using Eq. 1:

$$\tau_{out} = \left[1 + 7.69 * \frac{(D*L)^2}{\tau_{in}^4}\right]^{-\frac{1}{2}} \quad [1]$$

In this equation, D stands for the dispersion, L for the optical path length, $\tau_{in}$ is the duration of the input pulse, and $\tau_{out}$ is the duration of the elongated pulse. We calculated that, by the time 200-fs laser pulses reached the cornea, they were elongated to 1.25 ps at 800 nm and to 0.5 ps at 1150 nm. Longer pulses, obtained by dispersive stretching of the pulse through the fiber spool, were calculated by assuming known dispersion characteristics of the fiber. At the cornea, their durations varied from 0.6 ns at 800 nm to 0.3 ns at 1060 nm.

Figure 5B:
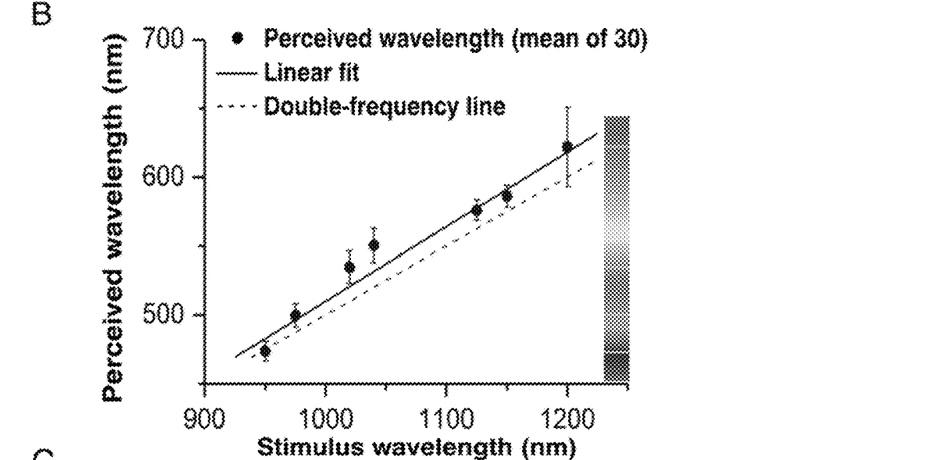

Some authors of the present paper perceived low energy IR laser radiation of 1060 nm as a pale greenish light. This novel experience engaged our interest in understanding the fundamental mechanism of human IR vision. To test whether a nonlinear optical process was involved, we exposed human eyes to 1 mW of pulsed laser radiation at 1040 nm and observed that green light perception was much stronger for pulsed light compared with CW (continuous wave) light of the same average power. Using a laser delivering 200-fs, 76-MHz excitation light, we were able to obtain consistent visible light sensation, strong enough to perform accurate color matching experiments. Using the experimental setup depicted in FIG. 1A, we then tested human visual responses to IR light. FIG. 5B shows the results of matching wavelengths of visible radiation to visual perception produced by an IR beam scanning the retinas of 30 healthy volunteers. All tested subjects detected the IR light. The data could be fit well with a linear function (solid line). The deviation from the frequency-doubled wavelength was noticeably larger for the points produced by 1020- and 1040-nm stimuli. These two well-perceived wavelengths also featured the largest SDs, with the exception of 1200 nm, where light perception was very weak due to increased absorption by water. These results suggest 2PO excitation or SHG as a mechanism contributing to visual color perception of IR light. If the SHG process was the only mechanism causing the perception of IR radiation as visible light, then the spectral width of the generated radiation should be roughly the same for every wavelength and coincide with the spectral width of the monochromator output, which transmits an 8-nm spectral bandwidth. This feature was observed for 950, 975, 1125, and 1150 nm, with SDs for these wavelengths at 7.2, 8.5, 7.4, and 8 nm, respectively, but not for 1020- and 1040-nm stimuli that had greater SDs (~12 nm). There are also other factors potentially influencing hue perception in color matching experiments, e.g., the Stiles-Crawford effect of the second kind.

Figure 5C:
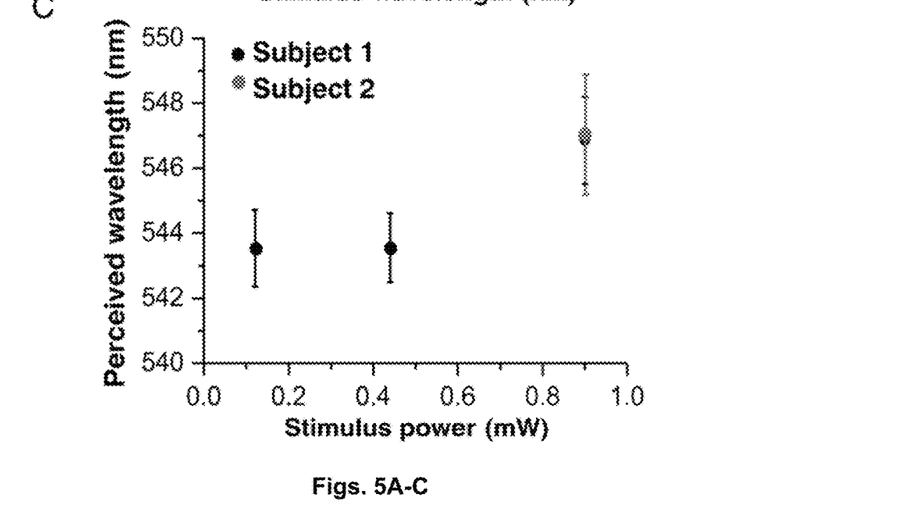

The reproducibility of our experiments was tested in two healthy volunteers (subjects 1 and 2) with a procedure of matching double frequency wavelength for 1040 nm repeated 10 times. Testing of subjects 1 and 2 was performed with a 0.9-mW IR light beam; tests of subject 1 were done additionally with 0.44- and 0.12-mW light beams (FIG. 5C). For higher powers of the applied laser beam, the perceived color seemed to be slightly red shifted. This observation could be explained by the additional contribution of red-shifted weak fluorescent light more easily detectable at increased optical power; however, this secondary absorption of emitted fluorescence could also occur in a 1PO excitation process.

To further investigate the nonlinearity of visual excitation, we conducted measurements of sensitivity to IR radiation (FIG. 6) using 0.3- to 0.6-ns (long) and 0.5- to 1.25-ps (short) laser pulses in two healthy subjects. We defined sensitivity as the reciprocal of the minimal power of the laser beam that still causes visual sensation. The beam was scanned horizontally at the fovea's height. For long pulses and wavelengths shorter than 1000 nm, our sensitivity results agreed with those previously obtained. We found the deviation from a monotonic decrease in sensitivity for wavelengths longer than 1000 nm. For excitation wavelengths shorter than 1040 nm, the perceived color of light was red. For excitation wavelengths longer than 1040 nm, the perceived color matched about half of the excitation wavelength. Wald's curve terminated at 1000 nm for the fovea and at 1050 nm for the peripheral retina, showing further decrease at 1050 nm equal to half an order of magnitude.

For short pulses, we found that changing the wavelength from 800 to 900 nm resulted in a decrease of sensitivity by ~3 orders of magnitude from $3.4 \times 10^7$ to $9.9 \times 10^4$ $W^{-1}$ for subject 1 and from $2 \times 10^8$ to $7.9 \times 10^5$ $W^{-1}$ for subject 2. This result is consistent with Wald and colleagues who found a decrease of sensitivity by 2.5 orders of magnitude for these wavelengths. For 1000 nm, Wald's group found a further decrease of sensitivity amounting to ~1.7 orders of magnitude (averaging fovea and periphery); our measurements for this wavelength show an increase of sensitivity to $19 \times 10^4$ $W^{-1}$ in subject 1 and only a slight decrease to $4.2 \times 10^5$ $W-1$ for subject 2 (FIG. 2). For excitation wavelengths shorter than 900 nm, the perceived color of light was red. For excitation wavelengths 950 nm and longer, the perceived color matched roughly half of the excitation wavelength.

To quantify the impact of a nonlinear process on inducing visual sensation, we varied the duty cycle by changing the laser pulse duration while keeping the pulse repetition frequency constant. We compared the minimum laser power needed for inducing visual sensation (sensitivity) when using long pulses with ~0.5-ns duration to that needed when using short pulses of ~0.9-ps duration (FIG. 2). Around 1000 nm (a region where a green light was perceived for short pulses and reddish for long pulses), the minimum laser power needed to evoke perception of light was more than 100 times larger for long pulses (on average $0.4 \times 10^{-3}$ W) than that needed for short pulses (on average $0.3 \times 10^{-5}$ W). This more than 100-fold increase in required laser power indicates the involvement of nonlinear processes in evoking IR light perception by the human eye. At wavelengths shorter than 900 nm, the difference in sensitivity to long and short pulses was small, indicating that a 1PO process is predominant for both long and short pulses in this region of wavelengths. Considering that absorption of IR by ocular tissue increases with increasing wavelengths, our results also show the optimal region, just above 1040 nm, for the human eye to perceive IR as light with colors corresponding to roughly half of the excitation wavelengths.

These two sets of results indicate that, depending on wavelengths, pulse duration, and laser power, we observed a combined effect of different physical processes: 1PO excitation, 2PO excitation, and perhaps SHG.

The above experiments were performed with foveal stimulation of the tested subjects and produced a color visual sensation, indicating that cones mediate IR vision.

To verify whether this process pertains to rods as well, we performed our visual tests on a person with documented autosomal recessive achromatopsia (ACHM). This individual also perceived IR beams of 950- and 1040-nm wavelengths. Here, visual perception was monochromatic, demonstrating the ability of human rods to detect IR light.

Example 2

Figure 8:
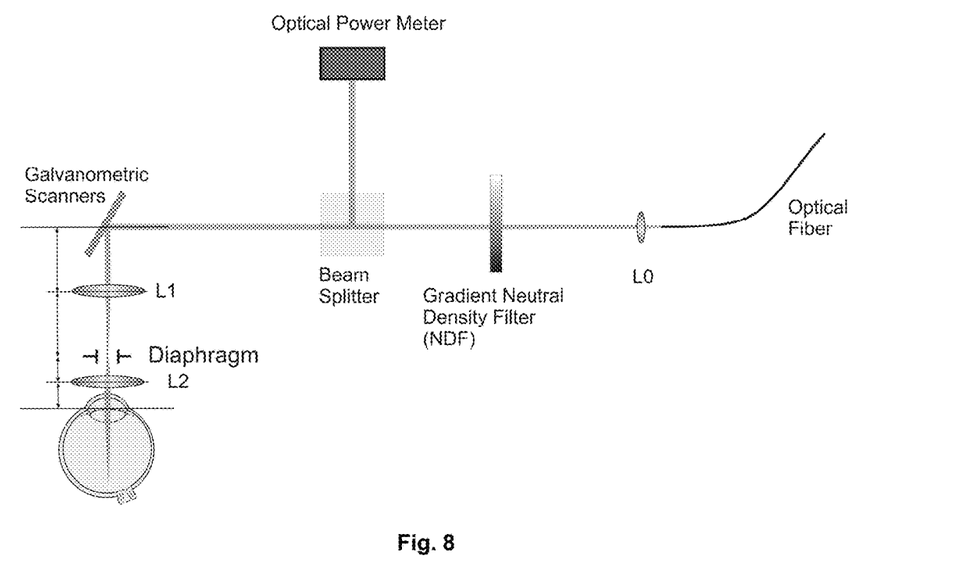
FIG. 8 is a schematic illustration of a two-photon ophthalmoscope for sensitivity measurements in accordance with one embodiment of the application.

A beam from a laser source emitting a 1040 nm train of 200-fs pulses was coupled into an optical fiber of 2 m or 1 km length to obtain the different pulse lengths, 1 ps or 300 ps, respectively. After the fiber, the test set-up was arranged to create a linear scan on the fundus, perceived by the volunteer as a horizontal line (FIG. 8). To measure minimal power of the laser beam causing a visual sensation (sensitivity threshold), a neutral density filter (NDF) filter was adjusted by the subject during the test. Values measured by the power meter were saved in PC memory after the subject pressed a mouse button and measurements were repeated 10 times.

The setup was isolated from residual ambient light by its dedicated housing, a subject's head was covered by a black curtain attached to the housing. All individuals were dark adapted.

The study was performed in 16 healthy volunteers of ages ranging from 24-84 years. All tests were conducted in compliance with ANSI Z136.1 and EN 60825-1. The study was approved by the Ethics Committee of the Collegium Medicum NCU. Examinations were carried out after written informed consent was obtained.

Results

Figure 9:
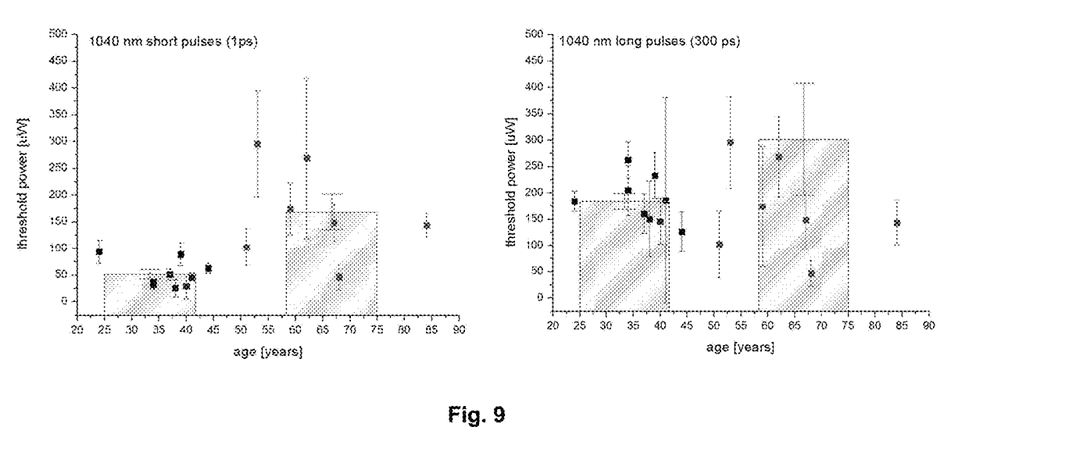
FIG. 9 illustrates a schematic graph showing sensitivity thresholds for a 1040 beam with different pulse lengths. Grey bars show mean values calculated for two sub groups of volunteers. <50 years old and >50 years old.

The results are presented in FIG. 9. Volunteers were divided into two groups differing in age. Mean threshold power values for short pulses of the two groups were: 52±8 µW for subjects of age <50 and 169±33 uW for the more elderly. For long pulses, means for both groups were: 184±44 µW and 300±280 µW, respectively. The one-way ANOVA test performed in the two groups with significance level ≤0.05 showed that the mean values were significantly different for short pulses but not for long ones.

This study indicated that the sensitivity threshold for human IR vision is age-dependent for short pulses. The two-photon absorption process is stronger for short pulses causing a statistically significant correlation with age.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A system for examination of an eye of a subject comprising:
   a laser for irradiating a selected portion of the retina with a short pulse light having a wavelength of about 1000 nm to about 1400 nm at an intensity effective to stimulate two photon induced isomerization of visual pigments in the selected portion of the retina of the subject's eye, and
   an input device to permit the subject to input a reaction due to the two-photon induced isomerization of visual pigments in the selected portion of the retina of the subject's eye to the irradiating light.

2. The system of claim 1, further comprising a controller capable of recording at least one of the following: a selected portion of the retina irradiated with the light, the reaction of the subject to the irradiating light, a time of the reaction, the intensity of the irradiating light at the time of the reaction, and the wavelength of the irradiating light at the time of the reaction.

3. The system of claim 2, wherein the controller compares the at least one threshold measurement or said partial threshold curve to corresponding values from a comparative database comprising a population of individuals, the controller storing said comparative database and the results of said comparing.

4. The system of claim 3, where the comparative database is stratified with respect to stratification criteria and the stratification criteria are used to select a defined group of individuals within said comparative database for use in said comparison step.

5. The system of claim 4, where the controller uses the results of the comparison to determine dark adaptation, photopic sensitivity, scotopic sensitivity, visual acuity, contrast sensitivity, color sensitivity, color discrimination, visual field or a combination of the foregoing of the subject.

6. The system of claim 3, where the status of the subject is considered impaired if one or more of said at least one threshold measurement or said partial threshold curve meets an impairment criterion.

7. The system of claim 6, where the impairment criterion is met when the comparing is conducted using a defined group from the comparative database consisting of healthy individuals and one or more of said at least one threshold measurement or said partial threshold curve falls outside of a reference range of corresponding measurements from the defined group.

8. The system of claim 7, where the impairment criterion is met when said comparing step is conducted using a defined group from the comparative database consisting of individuals diagnosed with a disease state and one or more of the at least one threshold measurement or said partial threshold curve falls within a reference range of said corresponding measurements from the defined group.

9. The system of claim 7 where the status of impaired is indicative of the subject having or at risk for a disease state selected from the group consisting of age related macular degeneration, vitamin A deficiency, Sorsby's Fundus Dystrophy, late autosomal dominant retinal degeneration, retinal impairment related to diabetes and diabetic retinopathy.

10. The system of claim 1, wherein the projecting device contains at least one of a galvo scanner, a resonant scanner, an amplitude mask, a phase mask, a modulating device as a chopper modulator or an optical modulator.

11. The system of claim 1, including means for choosing selected portions of the retina to be stimulated.

12. The system of claim 11, including means for identifying the selected portion on an image of the retina.

13. The system of claim 1 further comprising at least one optical element selected from the group consisting of a shaping optic to shape the irradiating light, a directing optic to direct the irradiating light, an optical splitter and a calibration detector.

14. The system of claim 1 further comprising a second light source for generating a bleaching light.

15. The system of claim 14 where said second light source is a light emitting diode, continuous wave (CW) laser, pulsed visible laser, or photographic flash equipped with an electronic strobe.

16. The system of claim 14, wherein the bleaching light has a wavelength about 500 nm to about 550 nm.

17. The system of claim 1, further comprising an alignment element to ensure the eye of the subject is properly aligned.

18. The system of claim 17, where the alignment element comprises at least one of an adjustable chinrest, a target fixation light, a fixation light or a camera to ensure and monitor proper alignment of the eye.

19. The system of claim 1, where the wavelength is about 1000 nm to about 1100 nm.

20. The system of claim 1, further comprising a scanning laser ophthalmoscopy device or optical coherence tomography device.

21. A method for examining an eye of a subject, the method comprising:
   irradiating a select portion of the retina of the eye with a short pulse light having a wavelength of about 1000 nm to about 1400 nm at an intensity effective to stimulate two photon induced isomerization of visual pigments in select portion of the retina the subject's eye, and monitoring a psychophysical response of the subject to the irradiating light.

22. The method of claim 21, where the psychophysical response comprises at least one of dark adaptation, photopic sensitivity, scotopic sensitivity, visual acuity, contrast sensitivity, color sensitivity, color discrimination, visual field or a combination of the foregoing.

23. The method of claim 21, where the method is used to determine a parameter selected from the group consisting of: the health of the subject's eye, if the subject is suffering from an eye disease, if the subject is at risk for developing an eye disease and the severity of an eye disease.

24. The method of claim 21, further comprising a recording at least one of the following: the reaction of the subject to the irradiating light, a time of the reaction, the intensity of the irradiating light at the time of the reaction and the wavelength of said irradiating light at the time of the reaction.

25. The method of claim 21, further comprising determining at least one threshold measurement or partial threshold curve from said recording.

26. The method of claim 21, further comprising comparing the at least one threshold measurement or said partial threshold curve to corresponding values from a comparative database comprising a population of individuals.

27. The method of claim 21, bleaching visual pigments in the retina prior to irradiating a portion of the retina with the short pulse light.

28. The method of claim 27, wherein the bleaching light has a wavelength about 500 nm to about 550 nm.

* * * * *